United States Patent [19]

Auer

[11] Patent Number: 4,691,829
[45] Date of Patent: * Sep. 8, 1987

[54] METHOD OF AND APPARATUS FOR DETECTING CHANGE IN THE BREAKOFF POINT IN A DROPLET GENERATION SYSTEM

[75] Inventor: Robert E. Auer, Miami, Fla.
[73] Assignee: Coulter Corporation, Hialeah, Fla.
[ * ] Notice: The portion of the term of this patent subsequent to Dec. 11, 2001 has been disclaimed.
[21] Appl. No.: 678,613
[22] Filed: Dec. 6, 1984

Related U.S. Application Data

[63] Continuation-in-part of Ser. No. 203,121, Nov. 3, 1980, Pat. No. 4,487,320.

[51] Int. Cl.[4] ............................................. B07C 5/342
[52] U.S. Cl. ..................................... 209/3.1; 209/579;
209/906; 346/75; 356/39; 356/72; 361/226;
364/413
[58] Field of Search .................................. 209/3.1–3.3,
209/44.1, 44.2, 546, 548, 549, 571, 579, 906, 127
R; 250/222.2; 356/39, 72, 73, 335, 338;
361/226; 364/413; 346/75

[56] References Cited

U.S. PATENT DOCUMENTS

| | | | |
|---|---|---|---|
| 3,380,584 | 4/1968 | Fulwyler | 209/3 |
| 3,710,933 | 1/1973 | Fulwyler et al. | 209/3.1 |
| 3,761,941 | 9/1973 | Robertson | 346/75 X |
| 3,826,364 | 7/1974 | Bonner et al. | 209/3.1 |
| 3,963,606 | 6/1976 | Hogg | 209/3 |
| 4,038,556 | 7/1977 | Auer et al. | 250/575 |
| 4,047,183 | 9/1977 | Taub | 346/75 X |
| 4,317,520 | 3/1982 | Lombardo et al. | 209/579 X |
| 4,318,480 | 3/1982 | Lombardo et al. | 209/3.1 |
| 4,318,482 | 3/1982 | Barry et al. | 209/579 X |
| 4,318,483 | 3/1982 | Lombardo et al. | 209/3.1 |
| 4,325,483 | 4/1982 | Lombardo et al. | 209/3.1 |
| 4,347,935 | 9/1982 | Merrill | 209/3.2 |
| 4,361,400 | 11/1982 | Gray et al. | 209/579 X |

OTHER PUBLICATIONS

H. R. Hulett et al., "Development and Application of a Rapid Cell Sorter", from Clinical Chemistry, vol. 19, No. 8, (1973), pp. 813-816.
Paul K. Horan et al., "Quantitative Single Cell Analysis and Sorting", from Science, vol. 198, pp. 149-157, Oct. 14, 1977.

Primary Examiner—Robert B. Reeves
Assistant Examiner—Edward M. Wacyra
Attorney, Agent, or Firm—Gerald R. Hibnick; Carl Fissell, Jr.

[57] ABSTRACT

A particle separator for sorting particles suspended in a liquid according to certain characteristics, including a method of and apparatus for detecting a change in the droplet breakoff point of a liquid jet stream which is subjected to vibrations. The vibrations produce amplitude undulations on the surface of the jet stream. The amplitude of the undulations is monitored or interrogated at a fixed point on the jet stream prior to the breakoff point. A change in amplitude of the undulations at that fixed point produces a signal voltage at a masked sense diode the value of which is proportional to the amplitude change. This signal voltage may be used (1) to alert the operator that a change has occurred in the point at which the jet stream is breaking up into droplets, (2) to automatically control the intensity of the vibrations for restoring the amplitude of undulation at that fixed point to its original state, or (3) to automatically disable the sorting portion of the apparatus. Any one or any combination of the foregoing three happenings can be utilized.

5 Claims, 15 Drawing Figures

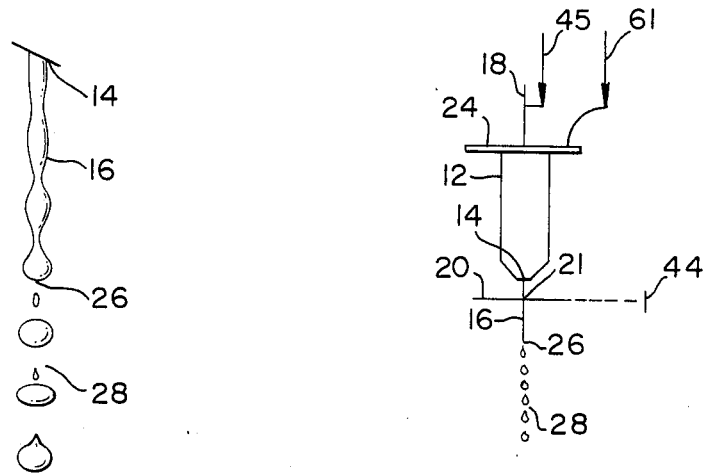
FIG-9.
FIG-10.
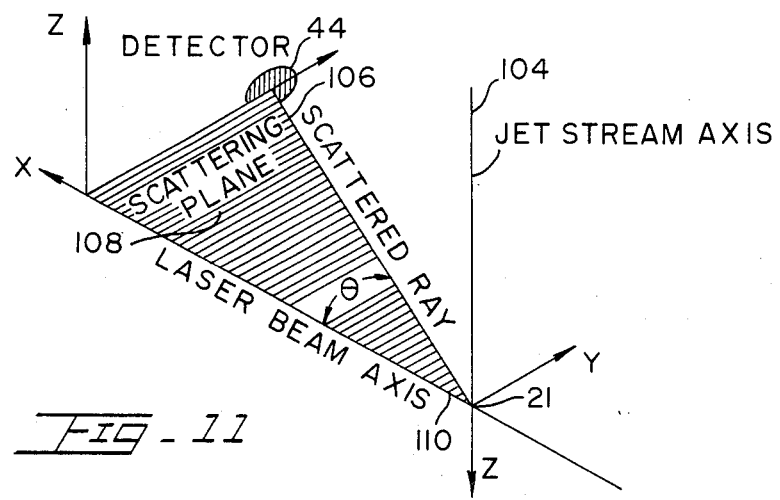
FIG-11.
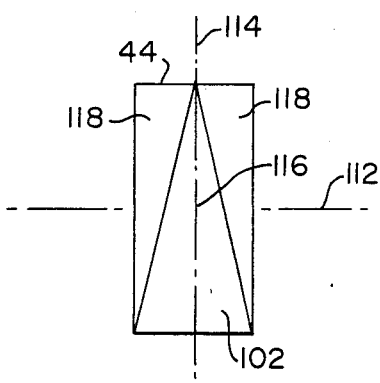
FIG-12.

4,691,829

METHOD OF AND APPARATUS FOR DETECTING CHANGE IN THE BREAKOFF POINT IN A DROPLET GENERATION SYSTEM

REFERENCE TO RELATED APPLICATIONS

This application is a continuation-in-part of Ser. No. 203,121 filed Nov. 3, 1980, now U.S. Pat. No. 4,487,320 issued Dec Apparatus For Detecting Change In The Breakoff Point In A Droplet Generation System".

This invention relates to apparatus for sorting minute particles in a fluid, and in particular to such apparatus wherein a liquid jet stream containing these particles is vibrated to produce undulations on the surface of the jet stream and subsequent break-up of the stream into droplets which are then sorted according to the particle characteristics and collected downstream.

BACKGROUND OF THE INVENTION

Apparatus of the foregoing kind may be referred to as flow cytometric sorting systems and are used in the medical research and diagnostic field for the rapid analysis of blood cells and other biological cells. Systems for cell separation and sorting are described in U.S. Pat. Nos. 4,038,556; 3,963,606; 3,710,933 and 3,380,584, in SCIENCE, Vol. 198, pages 149–157, published Oct. 14, 1977, and in the references cited therein.

U.S. Pat. No. 4,038,556 discloses a method of and apparatus for the simultaneous optical measurement of several characteristics of each particle of a group of small particles while the particles are suspended in a liquid.

U.S. Pat. No. 3,963,606 discloses a particle separator for separating particles in a liquid according to certain characteristics including a device for adjusting an electrical delay to be equal to the time between the emergence of a particle from a jet forming aperture to the breakoff point.

U.S. Pat. No. 3,710,933 discloses an apparatus for automatically analyzing and sorting minute particles suspended in a liquid on the basis of certain preselected characteristics.

U.S. Pat. No. 3,380,584 discloses a particle separator in which electrical pulses cause an acoustic coupler driver to vibrate the fluid which contains the particles.

The SCIENCE article, Vol. 198, pages 149-157 discloses a flow cytometer. Fluorescence from biological cells within a fluid stream is measured at the intersection with a laser beam. Droplets containing cells of interest are sorted out of the fluid stream. To the extent that it might be necessary to understand fully the techniques involved and the teachings of the invention herein, the above patents are incorporated herein for reference.

A major problem in using the cell sorter systems wherein a jet stream subjected to vibrations breaks off into droplets is ascertaining if a change has occurred in the point at which the jet stream is breaking into droplets. If the precise instant of breakoff with relation to the sense point changes, then the instrument ceases to be a cell sorter and becomes a water or saline solution sorter of unknown cell content. An even worse undesired result is that the unwanted particles are sorted when there is such a change in the breakoff point. Such a change is often due to changes in the mechanical coupling coefficients, such as air bubbles entering the flow chamber and partial plugs of the jet stream exit orifice. Optical sensitivies, such as the presence of undesired light, render impractical the use of an illuminating strobe source to observe the breakoff point on the jet stream while the system is taking data or sorting the cells. It is at this time of sorting that a monitor is most needed.

Furthermore an additional problem exists with respect to the sense diode used in detecting such change in the breakoff point. When the radiation beam which provides information concerning said changes is constructed and arranged so that the radiation beam moves on and off the sense means, and in particular, when the beam is totally on or off it, a saturation effect results and the signal produced by the sense means becomes constant thereby limiting the range of useful measurements.

OBJECTS OF THE INVENTION

An object of the present invention is to sense in a droplet generation system a change in the amplitude of the undulations at a fixed point on the surface of a liquid suspension jet stream prior to the droplet breakoff point, and to indicate that such a change has occurred.

Another object is to automatically disable the sorting function in a particle analyzer and sorting system when there is a significant change in the droplet breakoff point.

A further object is to utilize the information derived from a change in the amplitude of undulation at a fixed point on the surface of a jet stream to restore the level of the amplitude of undulation at that fixed point to its original state.

A still further object of the present invention is to provide an improved apparatus for detecting change in the breakoff point which has an increased range of useful measurements.

Other objects will appear from a reading of the detailed description of the invention.

SUMMARY OF THE INVENTION

The liquid jet stream containing the minute particles in suspension is driven at the frequency at which it is desired to generate droplets, normally 20 to 40 KC depending on the diameter of the jet exit orifice; for example, 32 KC frequency for a 76 micron jet exit orifice diameter and 40 KC frequency for a 50–60 micron jet exit orifice diameter. The jet is vibrated by introducing a small disturbance, as from a driven piezo-electric crystal, at the exit orifice of the jet stream. This disturbance is in the form of an undulation or a standing wave on the surface of the jet stream and this undulation grows as the jet advances and causes the breakoff of droplets downstream. The amplitude of the disturbance or undulation at any point along the jet stream is a function of the distance of that point from the point of droplet breakoff and this aspect is described in the report of Richard G. Sweet, SEL-64-004, March 1964, of the Stanford Laboratories of the Stanford University. According to the invention, the amplitude of the undulation at a fixed point is monitored. A change in this amplitude at that fixed point indicates a change in the breakoff point. A laser beam, used as the illumination source in the optical cell sorting systems described in the foregoing U.S. patents, is also utilized as a concentrated source of interrogating light rays in the monitoring scheme of the invention. The interrogating laser beam strikes the jet stream at a fixed point and then the laser beam scatters to provide a lobe pattern of scattered light that is in the same plane as the laser beam and is perpendicular to the jet stream. As is well known, this scattered laser light is modulated by the surface undulations on the jet. Heretofore, this modulation has been considered to be an undesirable phenomenon when cell light scatter is being measured and has usually been blocked out in the instrument. The present invention detects such modulation by positioning a photodiode in the plane of laser light scatter, hereinafter also referred to as the scattering plane. The output of the photodiode is converted to a voltage which may be used (1) to alert the operator either visually or audibly that a change has occurred at the point at which the jet stream is breaking up into droplets, (2) to automatically control the intensity of the vibrations applied to the jet for restoring the amplitude of undulation at the point on the jet at which it is being monitored, or (3) to automatically disable the apparatus. Any one or any combination of the foregoing happenings can be utilized in the practice of the invention.

If desired, a "secondary source" of concentrated light rays other than the laser beam used for sorting can be used to separately interrogate the jet stream and such secondary source can, if desired, be positioned so as to interrogate the jet stream by impinging thereon at a point closer to the droplet breakoff point where the undulations are larger and, therefore, where the signal obtained therefrom is larger. In this case, the photodiode would be judiciously positioned to receive the light scattered or reflected from the jet.

A feature of the invention is the sorting disabling circuitry which includes a fast change detector responsive to a rectified output whose D.C. level is proportional to the percentage modulation of the beam of concentrated light rays (laser beam, for example) as affected by the undulations on the surface of the jet stream. This detector controls a relay driver latching mechanism which acts to disable the sorting function of the particle analyzer whenever there is a significant change in the amplitude of undulation on the jet stream. This circuitry is provided with an operator reset device and an alarm which, if desired, can indicate the type of change based on the polarity of the output from the fast change detector.

Another feature is an automatic gain control (AGC) loop system for varying the intensity of the vibrations applied by the piezo-electric crystal to the jet stream, for slow changes in the amplitude of modulation. The foregoing-mentioned rectified output serves as a control voltage for the AGC loop. This loop system varies the power which is applied to drive the piezo-electric crystal. As a result, fine, as distinguished from coarse, amplitude corrections on the surface of the jet stream is obtainable. An arm-disable control for the AGC system enable initial setting of the droplet breakoff point.

An additional feature of the invention is to provide a masked sense photodiode whose sensitivity changes in a known manner with respect to position and which is large enough to always receive the light scattered from the jet.

BRIEF DESCRIPTION OF THE DRAWINGS

FIG. 9 illustrates in side elevation, to scale, the breakup of a regularly disturbed fluid jet stream;

FIG. 10 is an enlarged side elevation view of the non-electronic portions of the system components to the left of the dot-dash line 10 of the block diagram of FIG. 1 and the sense means 44;

FIG. 11 schematically illustrates the laser light being scattered from the surface of the jet stream 16 and being detected by the sense means 44 of the system shown in FIGS. 1 and 10;

FIG. 12 is an enlarged front elevation view of sense means 44 used in the system shown in FIGS. 1, 10, and 11;

Throughout the figures of the drawings the same parts are designated by the same reference numerals.

DESCRIPTION OF PREFERRED EMBODIMENT

Figure 1:
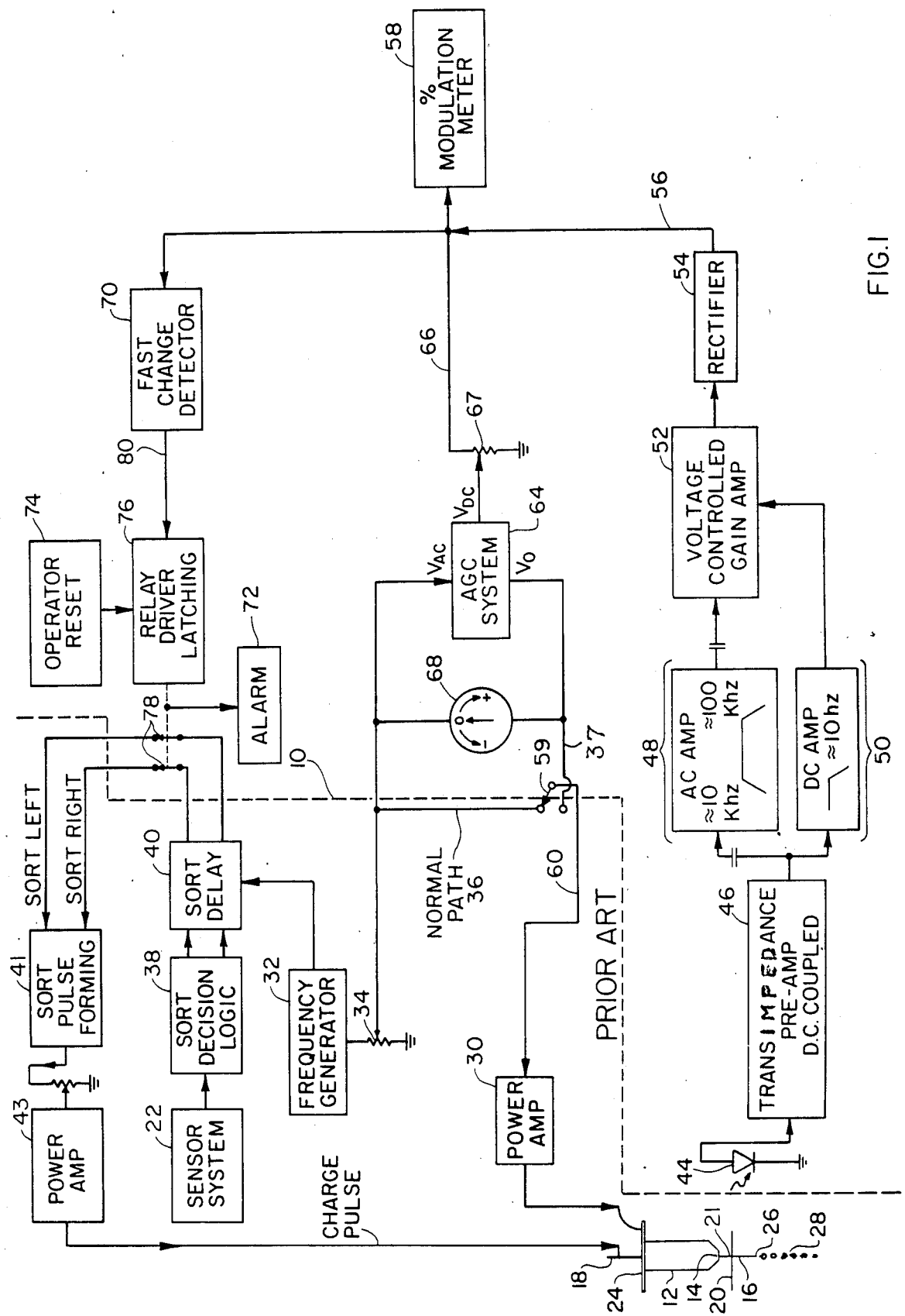
FIG. 1 is a block diagram showing how the electrical elements of the invention are coupled to a known type of particle analyzer and sorter.

The block diagram of FIG. 1 is divided into two parts by a dot-dash line 10. System components to the left of the dot-dash line are those which normally exist in a known type particle analyzer and sorting system, sometimes referred to as a flow cytometric sorting system. One such known sorting system is found in the TPS and EPICS ® series of instruments manufactured and sold by Coulter Electronics, Inc. of Hialeah, Fla. 33010. Only those components of the particle analyzer and sorter have been shown which are necessary to explain the operation of the present invention. System components to the right of the dot-dash line 10 comprise parts of the present invention which have been added and couple to the known particle analyzer and sorter for achieving the objects of the invention. It should be noted that the automatic gain control (AGC) feature and the disabling feature involving a relay driver latching mechanism of the invention are inserted at two locations into the normal signal paths of the particle analyzer and sorting system as will appear in more detail hereinafter.

The known particle analyzer and sorting system shown to the left of the dot-dash line 10 will now be briefly described. It includes a flow chamber 12 into which a saline solution (normally 13 p.s.i.g) is introduced under pressure and exits through a small orifice 14 (diameter ranges from 50μ to 200μ, depending upon the application of the system) to form a liquid jet stream 16 all of which is referred to as a first means for producing a jet stream. The sample (a suspension of minute particles, such as blood cells or biological cells) is introduced into the flow chamber 12 through a tube 18. Below the exit orifice 14 and above and prior to the breakoff point, the jet stream 16 is interrogated at a fixed sense point 21 by a light source or radiation means 20 (normally a laser beam) and the response of the minute particle in the sample to the illumination (normally light scatter and fluorescence) is detected by the sensor system 22 also at a point prior to and above the breakoff point.

The flow chamber 12 is mounted to and supported by a single vibrating means or second means for controlling the position of the breakoff point, a piezo-electric crystal assemblage 24, positioned above the radiation means 20, which vibrates the chamber 12 at a high frequency. The exact frequency at which the chamber 12 vibrates is dependent on the selected diameter of the exit orifice 14 which frequency is normally 20-40 KC. These vibrations impart small disturbances, normally undulations, on the surface of the jet 16 which grow, due to well known surface tension effects, and eventually pinch the jet off at a breakoff point 26 into well defined droplets 28. The breakup of a regularly disturbed fluid jet stream is shown in FIG. 9 and is included solely to illustrate such effects. The exact distance from the nozzle containing the orifice 14 to the breakoff point 26 is inversely proportional to the amplitude of the initial disturbance or undulation. The size of the disturbance is proportional to the amplitude of the signal voltage applied to the crystal 24, if the mechanical coupling coefficients of the system hold constant. Unfortunately, there are several factors which can cause changes in the mechanical coupling coefficients and these factors are difficult to eliminate. These include air bubbles entering the flow chamber 12 with the sample or with the saline solution and partial plugs of the exit orifice 14 due to debris, such as broken-up cells or fat.

The piezo-electric crystal is driven by a power amplifier 30 which normally derives its signal from a frequency generator 32 through a variable potentiometer 34 which is used to vary the amplitude of the signal applied to crystal 24 and therefore vary the nominal breakoff point 26. Potentiometer 34 serves as a coarse correction source to the drive of power amplifier 30 driving the crystal 24. Line 36 designates the normal path from the potentiometer 34 to the power amplifier in the absence of the components of the present invention. The system of the present invention has incorporated a switch 59 which is not present in the prior art systems, for a purpose described hereinafter.

Connected to the sensor 22 is the sort decision logic 38 in which the signals obtained from the detectors (not shown but forming part of the sensor system 22) are applied to a set of criteria to decide whether or not it is desired to capture the particle originating those signals. If capture is desired, that decision must be delayed, as by sort delay 40, while the particle travels from the sense point to the breakoff point. A sort pulse is then formed by sort pulse forming circuit 41 and amplified and applied, through power amplifier 43, over path 45 to the jet stream as a voltage just as the droplets which will contain the desired particle breaks off from the jet. Because of this impressed voltage the droplets break off with a net charge. The jet of droplets passes through an intense constant electric field which accelerates the charged droplets in the horizontal plane as they travel downwards. Thus charged droplets travel in a different path from the path of uncharged droplets and fall into different capture vessels, thereby effecting a physical sorting of the particles. A typical rate of sorting for this process is 4,000 particles per second. Reference is made to U.S. Pat. No. 3,380,584 which discloses a way of impressing a voltage on a downstream portion of the jet stream containing particles to be charged for subsequent collection and to an article by Hulett, Bonner, Sweet and Herzenberg, CLINICAL CHEMISTRY, Vol. 19, No. 8, 1973, which discloses impressing a voltage on an upstream portion of the jet stream for the same purpose.

The foregoing system is known in the art and no claim is made herein to this prior art method of analyzing and sorting minute particles. Such apparatus is disclosed in the aforementioned U.S. patents and the references cited therein.

The present invention makes use of the relationship between the amplitude of undulation on the surface of the jet stream at any fixed point and the position of the droplet breakoff point to ascertain that there has been a change in the droplet breakoff point. As stated hereinabove, the amplitude of the undulations increases as the breakoff point is approached. An increase in amplitude of undulation at any given point along the jet is an indication that the breakoff point is closer while a decrease in the amplitude is an indication that the breakoff point is further away. The apparatus of the present invention monitors the position of the breakoff point to effect any one of the following three results: (1) to provide an indication, either visually, as by means of a meter, or audibly, by means of an alarm, of a change in the breakoff point, (2) to disable the sorting process and sound an alarm if there is a fast change in the breakoff point, or (3) to automatically and promptly restore the breakoff point, as by means of an automatic gain control loop, for small and slow changes in the breakoff point.

The system components to the right of the dot-dash line 10 of the block diagram of FIG. 1 comprise parts of the present invention which couple to the known particle analyzer and sorter appearing at the left of dot-dash line 10, and include a photodiode or sense means 44 which detects the light scattered by the jet stream 16 as a result of the impact thereon by the concentrated beam of intense interrogating light 20 which light is preferably from the same laser used for sorting. Such photodiode 44 is preferably positioned in the scattering plane at an angle of approximately 39 degrees from the laser beam's axis. An enlarged view of the non-electronic portions of the system components to the left of the dot-dash line 10 of the block diagram of FIG. 1 and the sense means 44 are shown in FIG. 10. This scattered light has two components: a D.C. component which is proportional to the size of the jet stream 16 and the power of the light beam 20 (the laser, for example); and an A.C. component which is proportional to the undulations on the jet stream 16 at the sense point 21, the fixed point on the jet stream 16 at which the interrogating beam of light strikes it or impinges thereon, and the power of the intense interrogating light beam 20 (the laser). The diode 44 is operated in the current mode, that is to say it is terminated in low impedance, thereby producing a linear optical power-to-current relationship and reducing the effects of diode capacitance for maximum electronic bandwidth. Photodiode 44 is coupled to a breakpoint control means which includes an operational amplifier 46 which is operated as a transimpedance amplifier. Amplifier 46 converts the current from the diode 44 to a voltage linearly. The output from the transimpedance amplifier 46 splits into an A.C. path including A.C. amplifier 48 and a D.C. path including D.C. amplifier 50.

The A.C. path 48 contains the basic information to be used in the practice of the invention, viz, the amplitude of the undulations on the jet stream. Because the amplitude of the undulation signals generated at the photodiode detector 44 are low, this signal is given considerable gain by the A.C. amplifier 48, of the order of $10^3$. In order to improve the signal-to-noise ratio in this A.C. path the bandwidth of the A.C. amplifiers is limited to the range of frequencies of oscillation applied to the piezo-electric crystal 24.

Since the size of the jet stream 16 is held constant during a test run of sample particles and is rarely changed, the D.C. component is proportional to the size of the jet stream 16 and the power of the laser 20, then a change in the D.C. level in the path including D.C. amplifier 50 can be considered to be a change in laser power. The signal through the D.C. path controls the gain of a voltage controlled gain amplifier 52 in the output of the A.C. path, thereby enabling the A.C. path signal to be normalized as to laser power, as a result of which recalibration of the apparatus is eliminated each time the power of the laser 20 is changed. Stated another way, the D.C. path removes the effect of a change in laser power from the measurement of the distance from the sensing point 21 to the breakoff point 26.

Figure 8:
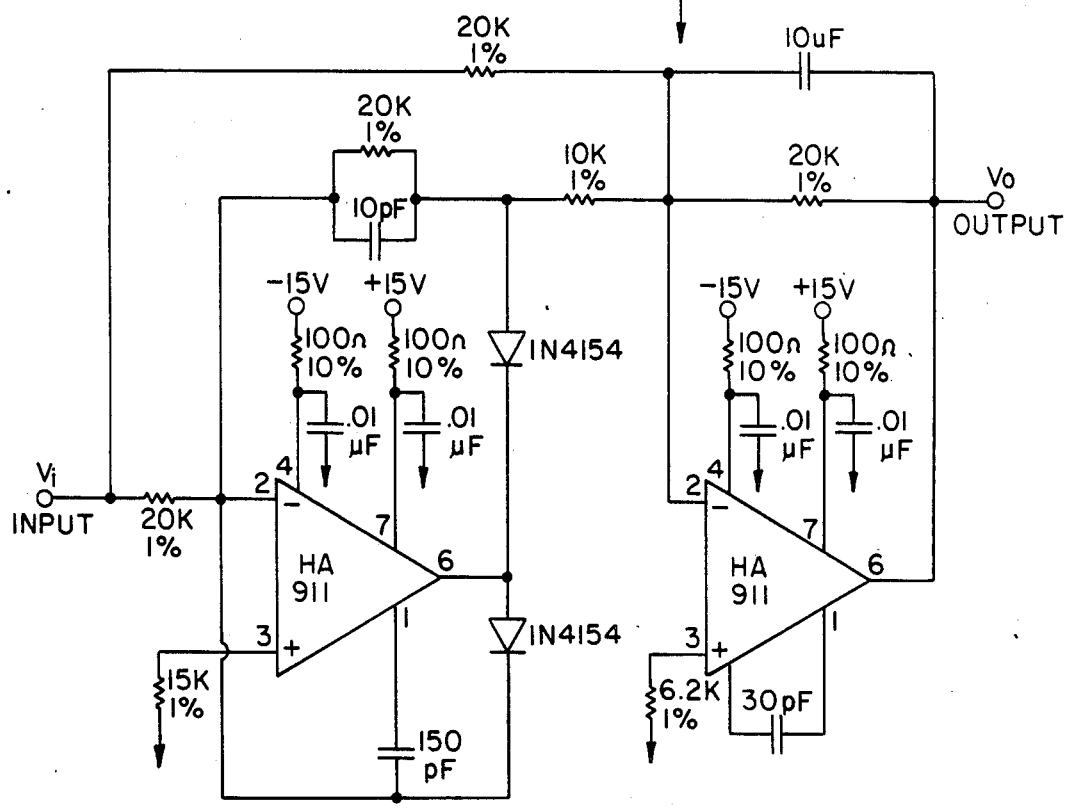

The A.C. signal from the voltage-controlled amplifier 52 is rectified by rectifier 54 (preferably a full-wave rectifier to obtain a smoother D.C. signal output therefrom) to provide a D.C. signal on lead 56 which is proportional to the amplitude of the undulations on the jet stream 16, and proportional to the distance from the sense point 21 to the breakoff point 26. The details of one suitable full wave rectifier which can be used is shown in FIG. 8.

The invention discloses three ways for utilizing the D.C. voltage on lead 56. The simplest is to drive a percentage modulation meter 58 which provides a visual indication as to the position of the droplet breakoff point 26 on the jet stream 16. Properly calibrated, such a meter 58 can be used to set the breakoff point 26 by manually adjusting a reference means or potentiometer 34 and using the normal path 36 in the known analyzer and sorter apparatus to bypass the AGC system hereinafter described. The meter 58 is connected so as to be operable at all times.

Figure 7:
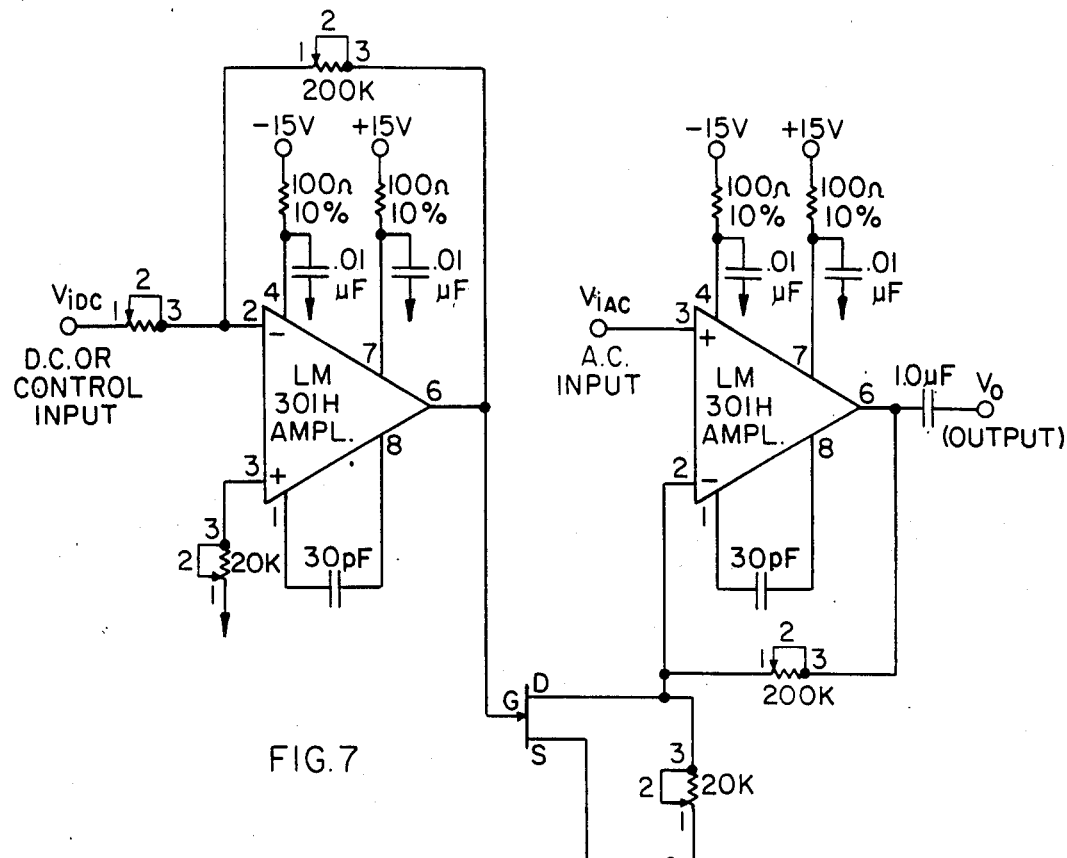

The rectified voltage on lead 56 (the output from rectifier 54) can also be used as a control voltage in an automatic gain control (AGC) loop which will provide fine, as distinguished from coarse, corrections over the path 60 to the voltage drive or power amplifier 30 which feeds the piezo-electric crystal transducer 24 over path 61, and therefore fine corrections in the drift in the breakoff point 26, assuming, of course, that control of the normal path 36 is transferred by switching means 59 when the AGC feature of the invention is utilized. This AGC loop includes an AGC amplifier system or control means 64 having an output, input and control terminals 65, 69 and 71, respectively, which is fed from the voltage on lead 56 over lead 66, and is similar in design to the circuitry of voltage controlled gain amplifier 52 as illustrated in FIG. 7. A suitable double pole-single throw switch 59 is connected across leads 36 and 37. Switch 59 serves to effectively deactivate the AGC loop from the system when it is desired to initially set up the analyzer and sorter for a specific droplet delay. After the proper time delay has been set, the AGC system 64 is armed or activated to maintain the desired breakoff point. Prior to activation of the AGC, the voltage output terminal $V_o$ (lead 37) is adjusted to the same amplitude as that on the normal path 36, by means of potentiometer 67 as is indicated by the null detection meter 68, after which switch 59 can be thrown to transfer control of the power amplifier 30 to the AGC system. The breakpoint control means also includes amplifiers 46, 48, 50 and 52, rectifier 54 and said control means 64 and reference means 34. The sensing means includes such breakpoint control means and the sense means 44.

Another way of monitoring the breakoff point 26 on the jet 16 is by means of a system including a fast change detector 70 to which the rectified voltage on lead 56 is fed. The output 80 of fast change detector 70 is zero if a D.C. signal is being applied (which is the case when the breakoff point 26 is constant) and changes from zero if a "fast" change in droplet breakoff point is encountered. The polarity of the change in the output 80 of the fast change detector 70 indicates whether the rectified signal level from rectifier 54 has increased or decreased. The output from detector 70 can drive an alarm circuit 72 to alert the operator of a change in the breakoff point. This same output can also drive a relay system composed of a driver latching mechanism 76, which, in turn, serves to automatically disable the sorting system, via leads 78 in the particle analyzer and sorter. Operator reset 74 serves to manually reset the driver latching mechanism 76. The alarm 72 can be made to indicate the type of change in the breakoff point based on the polarity of the output from the detector 70.

Figure 2:
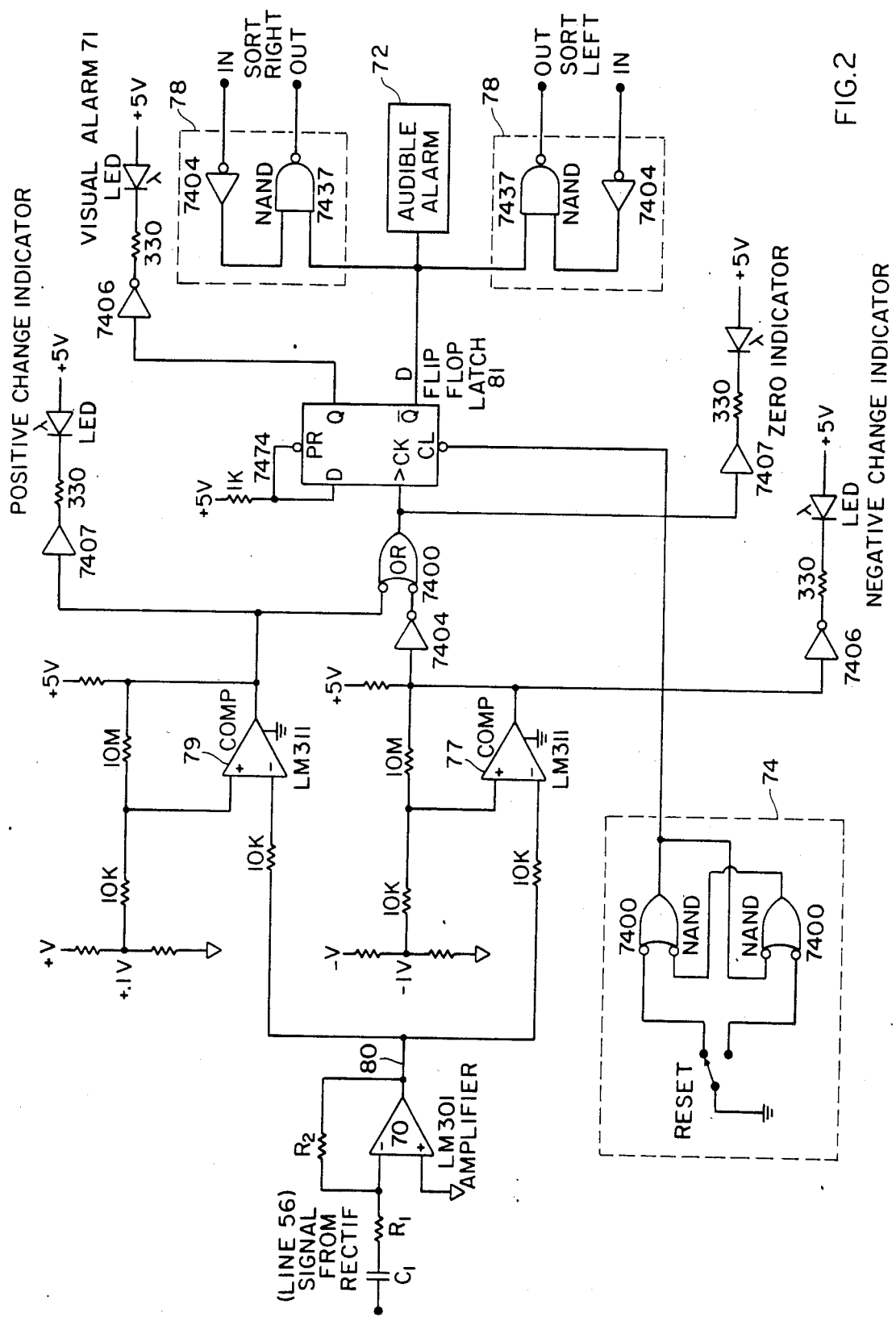
FIG. 2 shows the electrical circuitry of the fast change detector, the relay driver latching mechanism and the alarm circuits of the diagram of FIG. 1.

FIG. 2 diagramatically illustrates one form which the electrical circuitry of the fast change detector 70 may take, including the relay driving mechanism and the operator reset and the alarm. FIG. 2 shows both the audible alarm 72 and a visual alarm 71. The change of the signal on lead 56 is coupled to the amplifier 70 by capacitor $C_1$. This A.C. signal is amplified and applied to lead 80. If the signal on lead 56 is a constant D.C. value lead 80 will be near zero potential. Lead 80 is connected to two comparators 77 and 79 which are configured to sense variations in the signal on lead 80 in either Polarity away from a zero potential. A slight guard band is used to allow for amplifier offset. When the signal on lead 80 changes, the appropriate comparator senses the change and switches. The switching is sensed and latched by the latch 81. The $\overline{Q}$ output of the latch 81 switches, disabling NAND gates in 78, thus interrupting the sort signals. The switching of the latch also activates both a visual alarm 71 and an audible alarm 72. The values of capacitor $C_1$ and resistor $R_1$ are selected for speed of change while $R_1$ and $R_2$ are selected for sensitivity to change.

Figure 3:
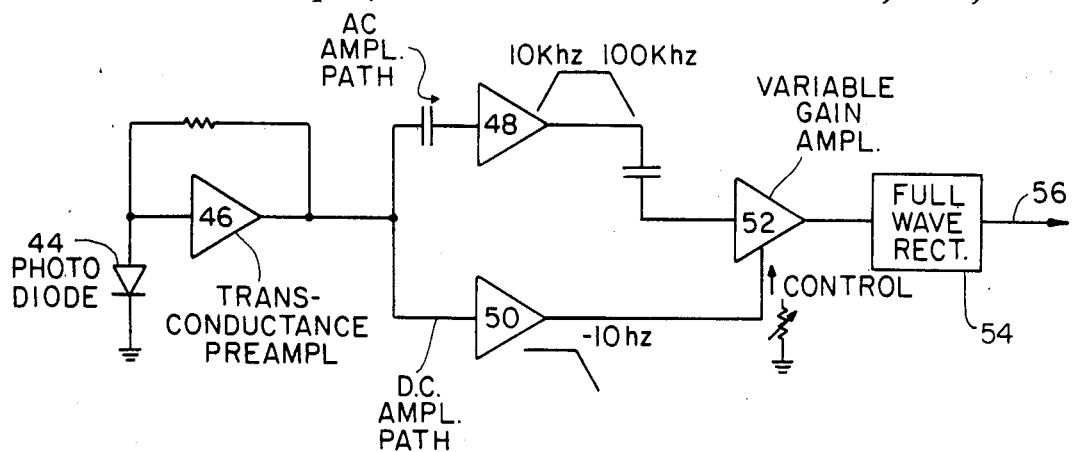
FIG. 3 shows diagrammatically the electrical circuitry for converting the signal obtained from the photodiode to a rectified D.C. which is proportional to the modulation of the light rays by the surface undulations on the jet stream.
Figure 4:
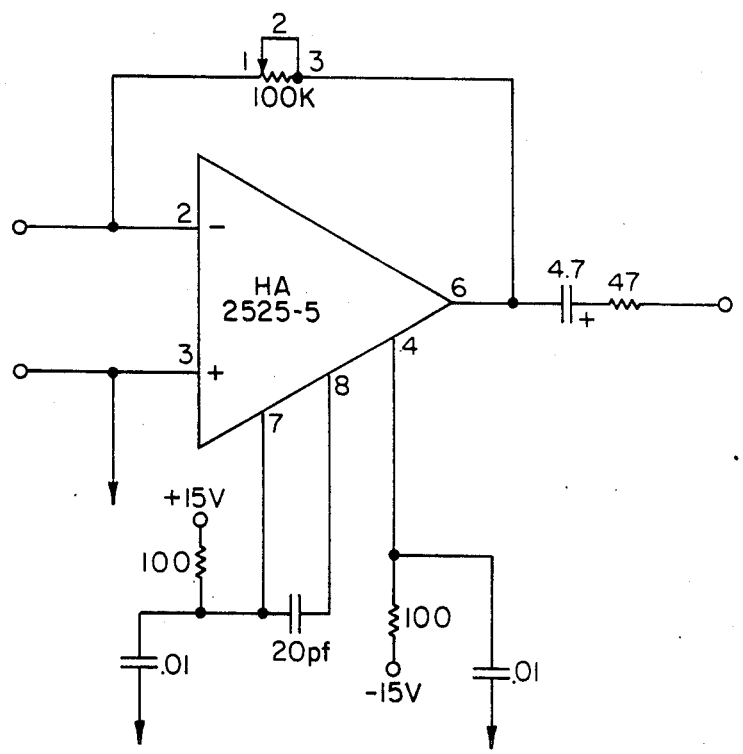
FIGS. 4 to 8 illustrate in more detail the electrical circuitry of the blocks shown in FIG. 3.
Figure 5:
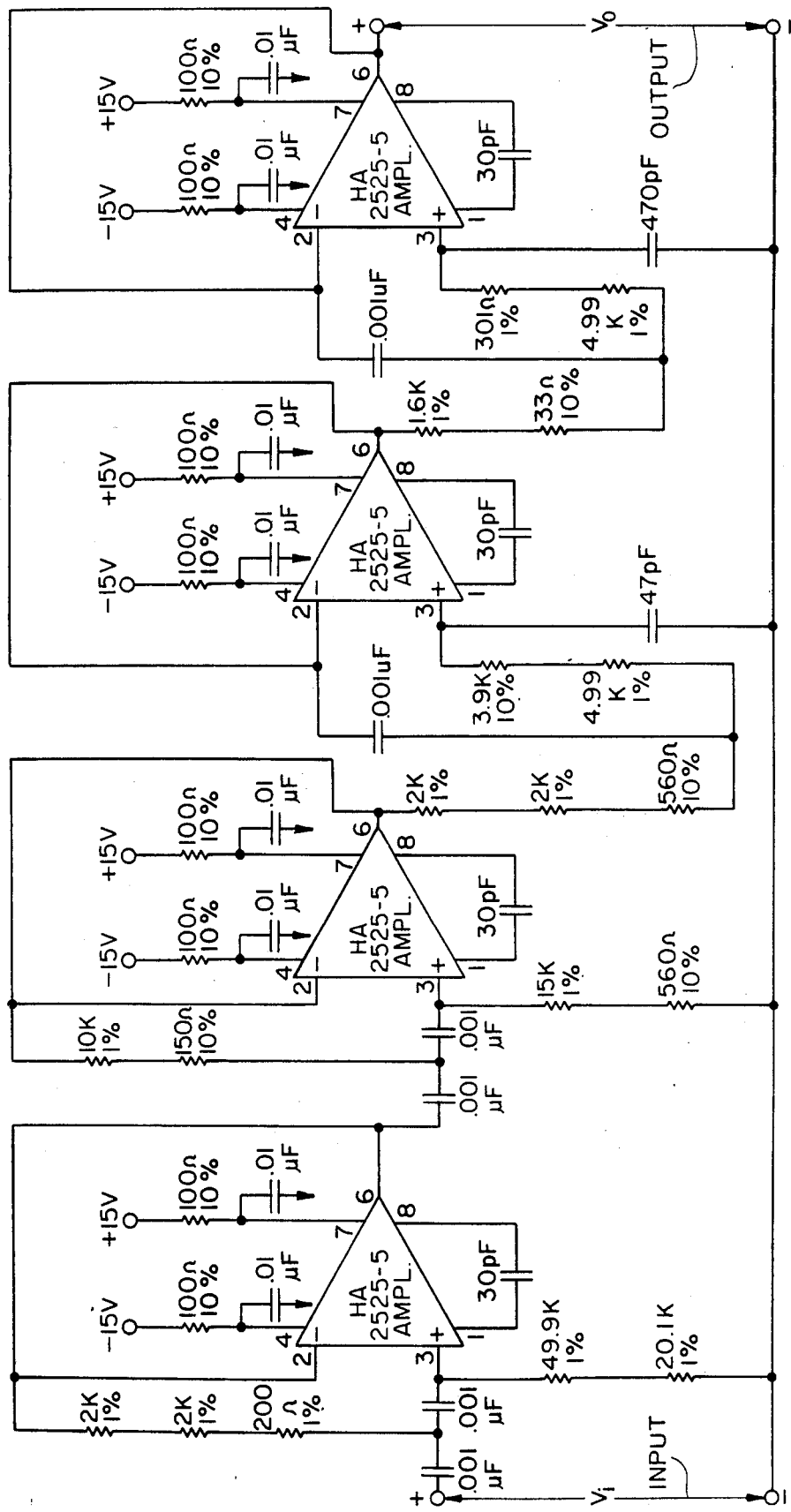
Figure 6:
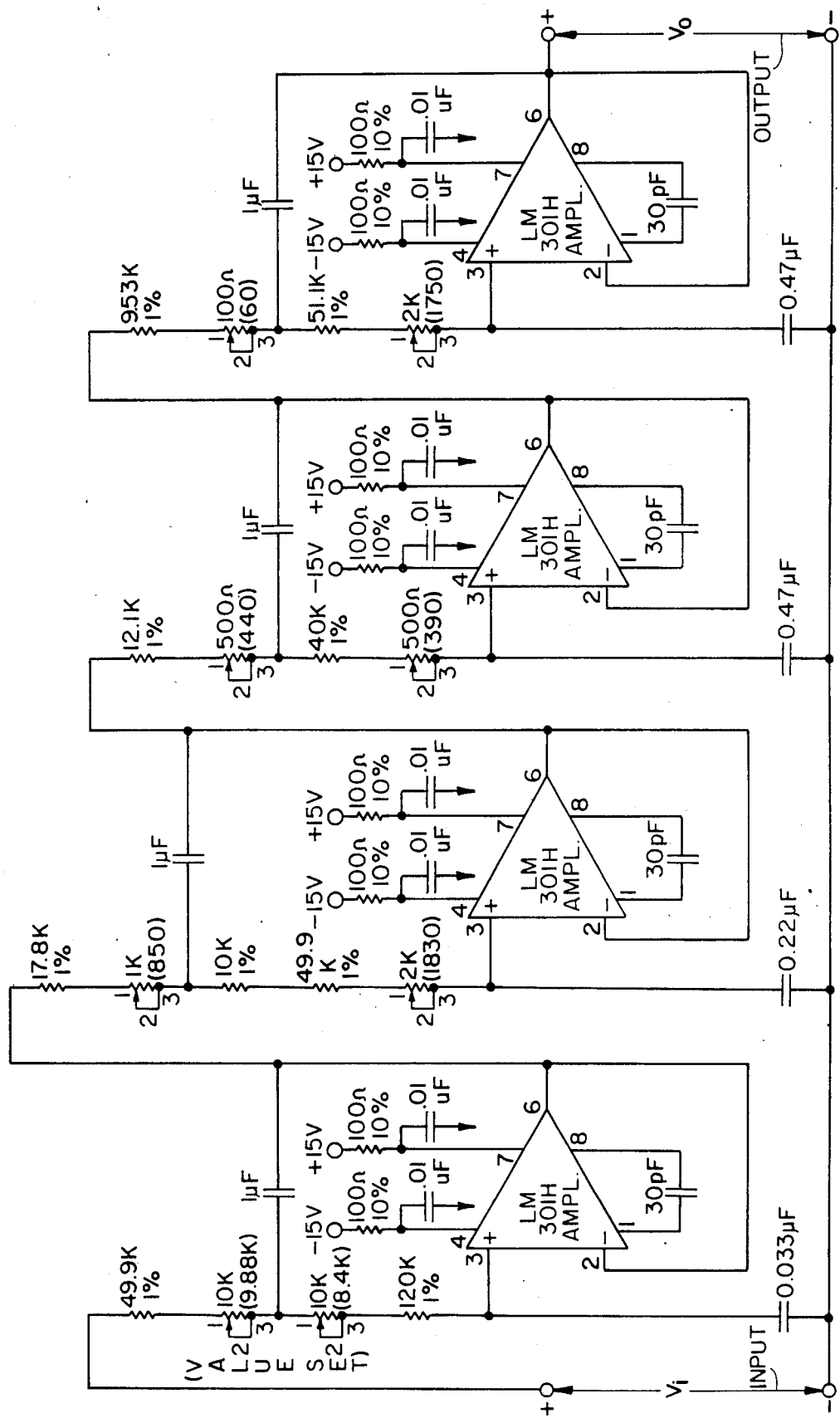

FIG. 4 illustrates the circuitry of the transimpedance pre-amplifier 46 of FIGS. 2 and 3. FIG. 5 illustrates the circuitry of the A.C. amplifier 48 of FIGS. 2 and 3. FIG. 6 illustrates the circuitry of the D.C. amplifier 50 of FIGS. 2 and 3. FIG. 7 illustrates the circuitry of the voltage controlled gain amplifier 52 of FIGS. 2 and 3. FIG. 8 illustrates the circuitry of the full wave rectifier 58 of FIGS. 2 and 3.

Figure 13:
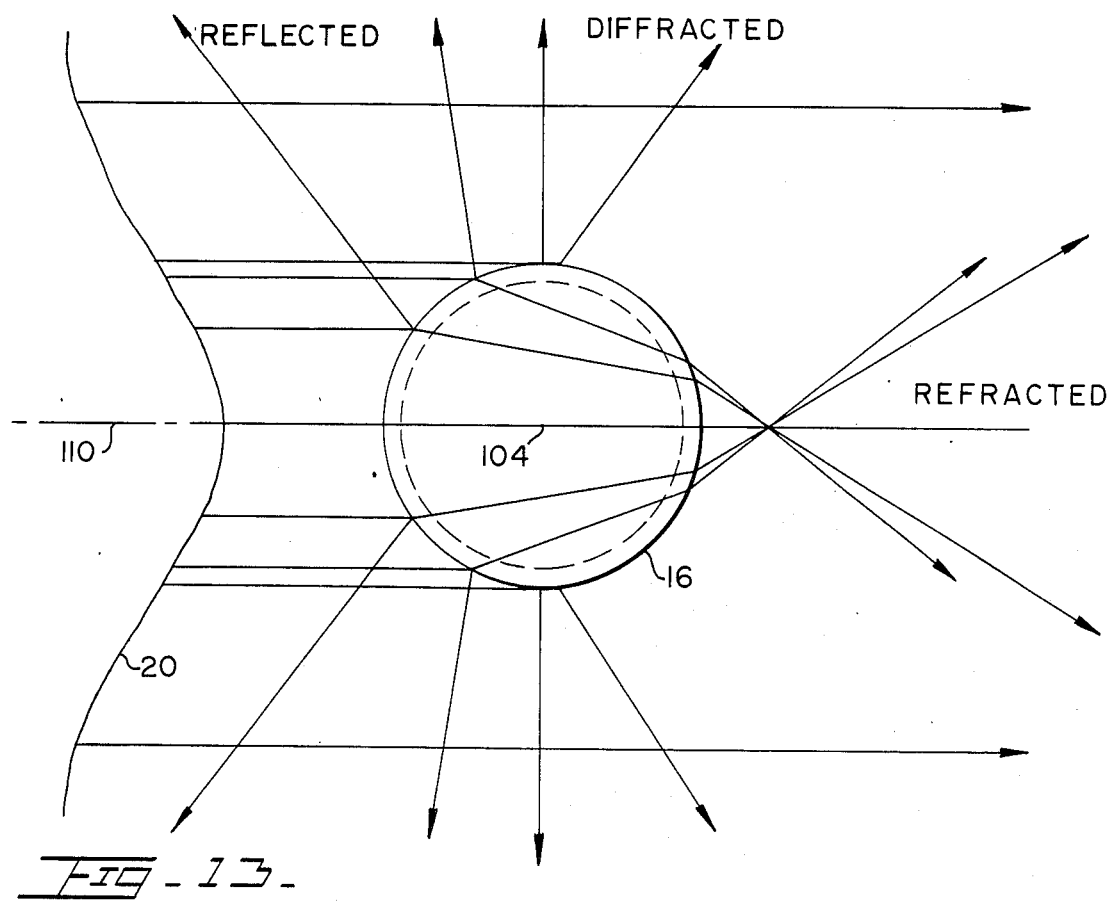
FIG. 13 is an enlarged, simplified, view of the laser beam impinging upon the sense point of the jet stream, in the X-Y scattering plane of FIG. 11, with the jet stream's minimum diameter shown in dot-dash, of the system shown in FIGS. 1 and 10.
Figure 14:
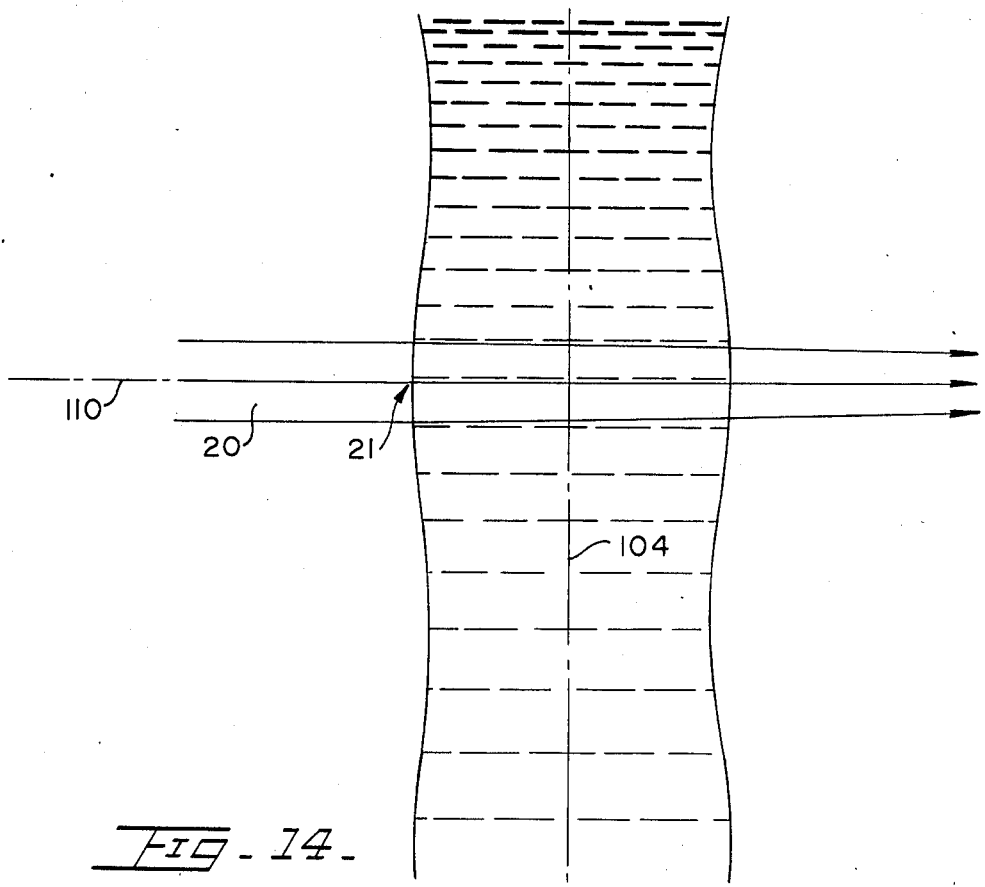
FIG. 14 is an enlarged, simplified, view of the laser beam impinging upon the sense point of the jet stream viewed in the X-Z plane of FIG. 11, when the jet stream is at its maximum diameter at the sense point, of the system shown in FIGS. 1 and 10.
Figure 15:
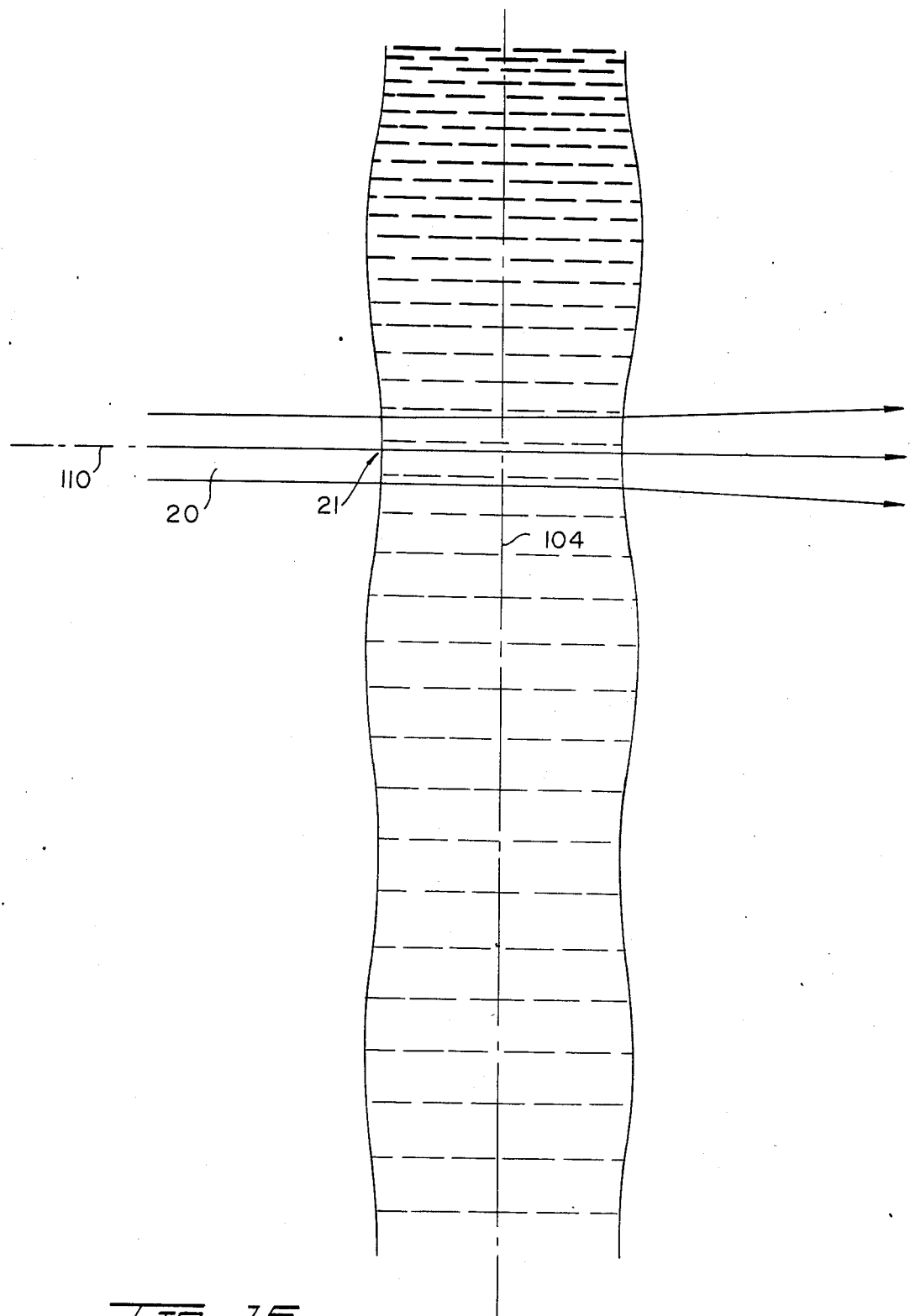
FIG. 15 is an enlarged, simplified, view of the laser beam impinging upon the sense point of the jet stream viewed in the X-Z plane of FIG. 11, when the jet stream is at its minimum diameter at the sense point, of the system shown in FIGS. 1 and 10.

Referring now to FIGS. 10–15 wherein the photodiode sense means 44, which is positioned in the scattering plane, has a masked configuration as shown in FIG. 12 and wherein its exposed and unmasked area or sensing surface 102 is located "generally" in the Y-Z plane and more particularly essentially radially of the jet stream's axis 104 as well as being perpendicular to the bundle of scattered rays, only one of which is shown, scattered ray 106, which ray 106 is located in the scattering plane 108, the X-Y plane. As particularly shown in FIG. 13 the laser's one over e squared beam 20 is on the order of twice the width of the jet stream 16 and its intensity profile is gaussian shaped. Furthermore, the laser beam 20 itself is generally elliptically shaped having a major axis and a minor axis and is focused so that its major axis lies in the scattering plane 108 and is perpendicular to the jet stream's axis 104 and its minor axis is parallel to the axis 104 of the jet stream 16. Referring now specifically to FIG. 13 the laser beam's longitudinal or central axis 110 is shown intersecting the longitudinal axis 104 of the jet stream 16. A portion of the interrogating laser beam 20 impinges on or upon the jet stream 16 at the sense point 21; another portion of the interrogating laser beam 20 goes directly by the jet stream 16 without impinging on it and is referenced to as the "direct" or non-impinging radiation. The impinging radiation produces scattered radiation having a lobe pattern and the mechanism of such radiation scatter includes reflection, diffraction and refraction, all of which emanate from the jet stream 16, and it is essentially the refracted radiation which is detected by the photodiode 44. A more detailed description of light scattering used in flow systems for cell sizing can be found in Chapter 5 of Flow Cytometry And Sorting, Edited by Melamed, Mullaney and Mendelsohn, published by John Wiley and Sons, 1979. Referring now particularly to FIGS. 14 and 15, since the sense point 21 is located upstream of the droplet breakoff point 26 (above the breakpoint region) where the amplitude of surface undulation on the jet stream 16 are essentially cylindrically or barrel shaped when viewed sideways or in the vertical or Z axis, the droplets within the jet stream 16 act as weak positive and negative lens; that is their radius of curvature is relatively large. The result is that the radiation which is incident upon the jet stream's surface and which is scattered by the jet stream 16 is converged and diverged only slightly along the vertical Z axis; that is, such scattered radiation is scanned in the vertical direction as shown. This effect is illustrated in said FIGS. 14 and 15 only for the refracted portion of the scattered radiation but its effect on the reflected and diffracted radiation is the same. The horizontal axis 112, FIG. 12 of the photodiode 44 is positioned to lie in a plane bounded by the laser beam's axis 110 and a line which intersects said laser's beam axis 110 and which is perpendicular to the jet stream's axis 104; this is the same as the scattering plane that would be formed if there were no undulations on the surface of the jet stream 16; that is the scattering plane's "resting" position. Its vertical axis 114 is disposed parallel to the jet stream's axis 104 and its center 116 would be preferably located at a point of maximum intensity of the scattered radiation in the resting scattering plane. Furthermore, the diode 44 is made sufficiently wide so that several maximum intensity points are encompassed thereby; these maximum intensity points or lines are due to the diffraction component of the scattered radiation. This scanning, as explained supra with respect to FIGS. 14 and 15, which is directly proportional to the amplitude of the jet stream's undulation, has been experimentally determined to be detected best by a masked diode as shown in FIG. 12 having a isosceles triangular shaped sensing area 102; the non-sensing areas are masked areas 118.

Although, as previously indicated, the photodiode 44 and its associated light source 20 can be moved to a point closer to the droplet breakoff point 26 where the undulations are larger, it cannot be moved to a point any closer to the breakoff point 26 which would result in the basic modulation information, the amplitude of the undulation of the jet stream 16, being lost; that is any point on the jet stream 16 beyond which would result in the output signal from the diode 44 no longer being proportional to the amplitude of the undulations on the jet stream 16. The portion of the jet stream 16 wherein such amplitude information is lost is referred to as the breakpoint region and all that portion of the jet stream 16 prior to or upstream to the actual breakoff point 26 is referred to as the uninterrupted portion of the jet stream 16.

Furthermore, although as previously indicated, approximately 39 degrees is the preferred angle for the sense photodiode 44, it may, if desired be placed at any angle in the scattering plane 108, including at zero degrees. In the later zero degree position a beam blocking means (not shown), configured to have the same dimensions as the laser beam's, would have to be appropriately disposed between the jet stream 16 and the photodiode 44 to permit only radiation scattering to be detected. This would require at least that their (the beam block and photodiode) centers be aligned with the laser beams axis 110, the photodiode 44, of course, having its sensing area extending beyond the periphery of the beam block.

The values of the components as well as the component parts illustrated in FIGS. 2 and 8 inclusive are merely illustrative and may be replaced by equivalent parts and circuitry to achieve the desired results.

The operative parameters of the preferred embodiment of the invention are as follows:

Jet stream 18 is driven at 32 KC for a 76 micron jet exit orifice diameter,

Sorting rate, at the high end, is 4,000 particles per second,

Distance from the jetting orifice 14 to the sense point 21 is on the order of 600 to 990 microns, Distance to breakoff point 26 from the sense point 21 is on the order of 5610 to 6600 microns, Diameter of jet stream 16 at sense point 21; maximum—68 microns, minimum—64 microns, Distance from jet stream 16 to sense diode 44 is approximately 500 jet diameters, Laser utilized, Argon Ion, Laser beam; major axis—150 microns, but may vary depending on the configurations of the shaping lenses, minor axis—16 microns, Sense diode 44; width 0.4 inches, height 0.8 inches, and Forward scatter particle sensor system 22 positioned so as to be coaxial with the laser beam axis 110.

Modifications can be made in the system of the invention without departing from the spirit and scope thereof. For example, since the A.C. path 48 contains the basic information constituting the amplitude of undulations on the jet stream, the D.C. path 50 need not be used in a simplified form of an embodiment of the invention.

What is claimed is:

1. In an apparatus for analyzing and sorting particles suspended in a liquid, said apparatus including first means for producing a jet stream from said liquid suspension, second means for vibrating said jet stream to produce undulations on the surface of said stream and subsequent breakup of said stream into droplets for collection downstream, said stream having a breakpoint region, the improvement comprising:

radiation means for impinging a beam of radiation upon an uninterrupted portion of said jet stream during its analyzing and/or sorting mode at a fixed location thereon prior to the breakpoint region, sensing means, coupled to said second means, responsive to radiation from said radiation means which is scattered by said stream, for providing an output to said second means which is proportional to the amplitude of undulation at said location, and wherein said second means is positioned above said radiation means.

2. In an apparatus for analyzing and sorting particles suspended in a liquid, said apparatus including first means for producing a jet stream from said liquid suspension, second means for controlling the position of the breakoff point, including vibrating means for vibrating said jet stream to produce undulations on the surface of said stream and subsequent breakup of said stream into droplets for collection downstream, said stream having a breakpoint region, the improvement comprising:

radiation means for providing a beam of radiation to interrogate a portion of said jet stream at a location thereon prior to the breakpoint region by impinging said beam thereon, and sensing means, coupled to said second means, responsive to radiation from said radiation means which interrogates said portion of said stream at said location, as a result of radiation scattered by said stream for providing an output which is a function of the amplitude of undulation at said location on said portion of said jet stream.

3. In an apparatus for analyzing and sorting particles suspended in a liquid, said apparatus including first means for producing a jet stream from said liquid suspension, second means for controlling the position of the breakoff point including vibrating means for vibrating said jet stream to produce undulations on the surface of said stream and subsequent breakup of said stream into droplets at a breakoff point for collecting downstream, said stream having a breakpoint region, the improvement comprising:

radiation means positioned below said vibrating means for impinging a beam of radiation upon said jet stream prior to said breakpoint region upon an uninterrupted portion thereof causing said jet stream to thereby scatter said radiation impinging thereon, and sensing means, coupled to said second means further including diode detection means having a masked and an unmasked area, said unmasked area being responsive to radiation impinging thereon scattered by said jet stream, for providing an output to said second means which is a function of the magnitude of the sensed scattered radiation and is proportional to the amplitude of undulation of said jet stream.

4. In an apparatus for analyzing and sorting particles suspended in a liquid, said apparatus including first means for producing a jet stream from said liquid suspension, second means for controlling the position of the breakoff point including vibrating means for vibrating said jet stream to produce undulations on the surface of said stream and subsequent breakup of said stream into droplets at a breakoff point for collecting downstream, said stream having a breakpoint region, the improvement comprising:

radiation means prior to said breakpoint region and below said vibrating means for impinging a beam of radiation upon an uninterrupted portion of said jet stream causing said jet stream to thereby scatter said radiation impinging thereon, and sensing means, coupled to said second means including diode detection means comprising a sensing area having a masked and an unmasked portion, said unmasked portion varying in extent in a predictable and monotonic manner and being responsive to the sensed radiation impinging thereon scattered by said jet stream, for providing an output to said second means which is a function of the magnitude of the sensed scattered radiation and is proportional to the amplitude of undulation at said portion of said jet stream.

5. In an apparatus for analyzing and sorting particles suspended in a liquid, said apparatus including first means for producing a jet stream from said liquid suspension, second means for controlling the position of the breakoff point including vibrating means for vibrating said jet stream to produce undulations on the surface of said stream and subsequent breakup of said stream into droplets at a breakoff point for collecting downstream, said stream having a breakpoint region, the improvement comprising:

radiation means prior to said breakpoint region and below said vibrating means for impinging a beam of radiation upon an uninterrupted portion of said jet stream causing said jet stream to thereby scatter said radiation impinging thereon, and sensing means, coupled to said second means including diode detection means comprising an isosceles triangular-shaped sensing area provided with a masked and an unmasked portion, said unmasked portion being responsive to the sensed radiation impinging thereon scattered by said jet stream, for providing an output to said second means which is a function of the magnitude of the sensed scattered radiation and is proportional to the amplitude of undulation at said portion of said jet stream.

* * * * *

UNITED STATES PATENT AND TRADEMARK OFFICE
CERTIFICATE OF CORRECTION

PATENT NO. : 4,691,829

DATED : Sept. 8, 1987

INVENTOR(S) : Robert E. Auer

It is certified that error appears in the above—identified patent and that said Letters Patent is hereby corrected as shown below:

Column 1, lines 7 and 8, delete "Ser. No. 203,121 filed Nov. 3,1980, now".

Column 1, line 9, after "issued" delete "Dec" and insert --December 11, 1984, and entitled "Method Of And--.

Column 8, line 45, change "Polarity" to --polarity--.

Signed and Sealed this

Fifth Day of January, 1988

Attest:

DONALD J. QUIGG

Attesting Officer

Commissioner of Patents and Trademarks